United States Patent [19]

Stief et al.

[11] Patent Number: 5,607,837

[45] Date of Patent: Mar. 4, 1997

[54] METHOD FOR THE DETERMINATION OF THE PLASMINOGEN ACTIVATOR ACTIVITY IN SAMPLES CONTAINING ALPHA-2-ANTIPLASMIN

[75] Inventors: Thomas Stief, Sevilla, Spain; Norbert Heimburger, Marburg, Germany

[73] Assignee: Behringwerke Aktiengesellschaft, Marburg, Germany

[21] Appl. No.: 96,843

[22] Filed: Jul. 26, 1993

Related U.S. Application Data

[63] Continuation of Ser. No. 454,470, Dec. 21, 1989, abandoned.

[30] Foreign Application Priority Data

Dec. 23, 1988 [DE] Germany .......................... 38 43 422.9

[51] Int. Cl.⁶ ............................................. C12Q 1/56
[52] U.S. Cl. ............................ 435/13; 435/18; 435/174; 435/23; 435/24; 530/300
[58] Field of Search ............................... 435/13, 18, 174, 435/23, 24; 530/300

[56] References Cited

U.S. PATENT DOCUMENTS

| | | | |
|---|---|---|---|
| 4,033,824 | 7/1977 | Karyes et al. ........................... | 435/13 |
| 4,177,262 | 12/1979 | Lormeau et al. ........................ | 530/380 |
| 4,563,420 | 1/1986 | Verheijen ................................ | 435/13 |
| 4,605,614 | 8/1986 | Nagasawa et al. ...................... | 435/13 |
| 4,710,459 | 12/1987 | Bartl et al. .............................. | 435/214 |
| 5,057,414 | 10/1991 | Stief ........................................ | 435/13 |
| 5,296,357 | 3/1994 | Keuper .................................... | 435/23 |

OTHER PUBLICATIONS

Moroz, Leonard A.; Mini–Plasminogen: A Mechanism for Leukocyte Modulation of Plasminogen Activation by Urokinase; Jul. 1981; Blood, vol. 58, No. 1, pp. 97–104.

Holvoet, Paul et al.; A Monoclonal Antibody Specific for Lys–plasminogen; Oct. 5, 1985; The Journal of Biological Chemistry, vol. 260, No. 22, pp. 12106–12111.

Chmielewska, J. et al.; Determination of Tissue Plasminogen Activator and Its "Fast" Inhibitor in Plasma; 1986; Clinical Chemistry, vol. 32, No. 3, pp. 482–485.

Berne et al, eds. *Physiology*. St. Louis., C. V. Mosby, 1988 pp. 382–385.

*Primary Examiner*—Carolyn Paden
*Attorney, Agent, or Firm*—Finnegan, Henderson, Farabow, Garrett & Dunner, L.L.P.

[57] ABSTRACT

The disclosed invention provides a method for determining the plasminogen activator (PA) activity in a biological fluid. The method involves the use of proteolytically-degraded plasminogen and effectively eliminates the influence of alpha-2-antiplasmin on the determination of PA activity.

8 Claims, No Drawings

METHOD FOR THE DETERMINATION OF THE PLASMINOGEN ACTIVATOR ACTIVITY IN SAMPLES CONTAINING ALPHA-2-ANTIPLASMIN

This application is continuation of application Ser. No. 07/454,470, filed Dec. 21, 1989, now abandoned.

BACKGROUND OF THE INVENTION

The invention relates to a method for the determination of the activity of plasminogen activators in plasma or other biological fluids.

The key enzymes in the physiological fibrinolysis in mammalian blood are the two plasminogen activators a) tissue plasminogen activator (t-PA) and b) urinary plasminogen activator (u-PA). Plasminogen activators convert the inactive zymogen plasminogen into the protease plasmin. Plasmin degrades insoluble fibrin into soluble fibrin split products.

The activity of these PAs in human blood is of great diagnostic relevance for measuring the fibrinolytic potential of a patient. The fibrinolytic potential provides information on, inter alia, possible thrombo-embolisms which are to be expected. However, PAs occur only in small amounts (ng/ml) in plasma. This makes great demands on the sensitivity and specificity of the detection method.

The functional determination of PAs according to the state of the art entails their natural substrate, plasminogen, and a chromogenic plasmin substrate being added to the sample. In this case, the measured plasmin activity represents PA activity which is enhanced in direct proportion.

However, the plasmin which is produced is immediately inhibited, almost quantitatively, by alpha-2-antiplasmin which is likewise contained in the sample, so that only low plasmin activity can be measured.

The accuracy of functional PA determination thus depends on eliminating this antiplasmin effect. The methods for the functional determination of PAs described in the state of the art therefore either provide for additional plasma separation steps such as euglobulin precipitation or require acidification and subsequent neutralization of a highly diluted sample. Both methods are relatively time-consuming and methodologically demanding.

SUMMARY OF THE INVENTION

Hence the object of the present invention was to provide a method with which the activity of PA in plasma, serum or other biological fluids can be determined rapidly and reliably. This object is achieved according to the invention by treating the plasminogen which is necessary for the determination of the PAs with a protease, preferably elastase, or with a serine protease, preferably plasmin or trypsin, particularly preferably elastase at pH 7–pH 8, or plasmin or trypsin at pH 10–13, until a molecule is produced which, after conversion into plasmin, is no longer inhibited by alpha-2-antiplasmin. An assay suitable for monitoring this reaction is, for example, "Berichrom® alpha-2-antiplasmin" from Behringwerke AG, Marburg, FRG. The exposure to these proteases can be carried out in such a way that they are present in immobilized form (for example coupled to $^R$Sepharose) and thus do not interfere in the activity assay which is to be carried out subsequently.

DESCRIPTION OF THE PREFERRED EMBODIMENTS

It has emerged, surprisingly, that in a method for the determination of PA the addition of plasminogen treated in this way allows the activity of PA to be determined without interference from alpha-2-antiplasmin.

The invention relates to a method for the determination of the plasminogen activator activity in a biological fluid containing alpha-2-antiplasmin, which comprises addition of proteolytically degraded plasminogen to this fluid, and determination of the resulting plasmin by means of a chromogenic substrate specific for plasmin. The invention is furthermore defined in the claims and explained in the examples which follow, without restricting the inventive concept.

EXAMPLE 1

Pretreatment of plasminogen with elastase-$^R$Sepharose and use in the detection of plasma PA activity.

3×80 CTA-U (Committee of Thrombolytic Agents Units) of plasminogen (Behringwerke assay plasminogen, Marburg, FRG) were dissolved in 7 ml of 50 mM tris/HCl, pH 8.4, and a) adjusted to pH 8.0, b) adjusted to pH 12.0 and c) left unchanged. One a) and one b) solution were passed at a flow rate of 30 ml/h through 1 ml of elastase-$^R$Sepharose (2.5 mg of protein/ml of gel bed, coupled by the method of Axen et al., Nature 214, 1302–1304, 1967). The flow-throughs were adjusted to pH 8.4 (solutions a) to c)), made up to 8 ml with 50 mMtris, pH 8.4, and used in a PA assay as follows:

50 µl of human citrated plasma which contained various amounts of alpha-2-antiplasmin, prepared by mixing normal plasma with plasma deficient in alpha-2-antiplasmin (prepared by immunoadsorption), were incubated with 200 µl of the above plasminogen samples and 200 µl of 5 IU/ml u-PA in 100 mMtris, 100 mMNaCl, 1% polygeline, 0.1% $^R$Tritonx 100 at 37° C. for 5 min. 500 µl of 0.6 mM chromogenic plasmin substrate HD-norvalyl-cyclohexyl-alanyl-lysyl-para-nitroanilide in 480 mM NaCl were then added, the substrate conversion was stopped after 5 min at 37° C. by addition of 100 µl of 8.5 M acetic acid, and the resulting extinction at 405 nm was determined. The same assay mixture with addition of only tris buffer without u-PA content was used for blank correction.

TABLE 1

| Content of alpha-2-antiplasmin % | plasminogen degraded with elastase-$^R$Sepharose | | untreated |
|---|---|---|---|
| | pH 8 | pH 12 | plasminogen (control) |
| | $A_{405nm}$/5 min (E × 1000)* | | |
| 100 | 910 ± 4 | 648 ± 5 | 107 ± 0 |
| 75 | 962 ± 1 | 676 ± 5 | 198 ± 17 |
| 50 | 1037 ± 3 | 771 ± 3 | 280 ± 1 |
| 25 | 1152 ± 2 | 860 ± 5 | 496 ± 1 |
| 0 | 1309 ± 3 | 1061 ± 4 | 749 ± 1 |

*Means of duplicate determinations

It is evident that when plasminogen which has not been pretreated is used the extinction (PA activity measurement) greatly depends on the alpha-2-antiplasmin content of the sample. This dependence is reduced by proteolytic pretreatment of plasminogen with elastase, preferably at pH 8.

When plasminogen which had been degraded at pH 12 was added, the extinction was 860±5 at an antiplasmin content of 25% and 648±5 at an antiplasmin content of 100%, that is to say only 25% less. The corresponding extinctions for the control are 496±1 and 107. This is a decrease of almost 80%.

EXAMPLE 2

Pretreatment of plasminogen with plasmin-$^R$Sepharose and use in the detection of plasma PA activity.

Plasminogen was dissolved as in Example 1, then a) and b) preparations were passed through 1 ml of plasmin-Sepharose (2.5 mg of plasmin/ml of gel), and flow-throughs and c) solution were made up to 8 ml (pH 8.4) and investigated in the PA assay as in Example 1.

TABLE 2

| Plasma content of alpha-2-antiplasmin % | Addition of plasminogen degraded with plasmin-$^R$Sepharose | |
|---|---|---|
| | pH 8 | pH 12 |
| | $A_{405nm}$/5 min (E × 1000)* | |
| 100 | 114 ± 2 | 554 ± 9 |
| 75 | 113 ± 1 | 591 ± 1 |
| 50 | 168 ± 3 | 644 ± 2 |
| 25 | 346 ± 4 | 749 ± 3 |
| 0 | 603 ± 0 | 937 ± 5 |

*Means of duplicate determinations
See Table 1 for control, because test mixture the same.

It is again evident that the dependence of the PA activity measurement on the antiplasmin concentration is greatly reduced by comparison with the control (Tab. 1) especially on pretreatment of plasminogen at pH 12 with plasmin.

We claim:

1. A method for the in vitro assay of the plasminogen activator (PA) activity in a biological fluid which contains alpha-2-antiplasmin comprising:

digesting plasminogen with a protease coupled to a carrier, wherein the protease is selected from the group consisting of elastase, plasmin, and trypsin;

separating the digested plasminogen from the said protease to provide a proteolytically-digested plasminogen source (P-DPS);

adding said P-DPS to the biological :fluid to be sampled for PA activity and allowing said P-DPS to be converted by the PA activity of the biological fluid into a resulting plasmin;

adding a chromogenic substrate specific for plasmin; and measuring any increase in optical density resulting from liberation of a chromophore produced as a result of the action of the resulting plasmin on the chromogenic substrate.

2. The method as claimed in claim 1, wherein said digestion is carried out at pH 7–8.

3. The method as claimed in claim 1, wherein said digestion is carried out at pH 10–13.

4. A method for determining PA activity in a biological fluid employing a proteolytically-digested plasminogen source (P-DPS), wherein said P-DPS is generated by digesting a plasminogen with a protease and the P-DPS is separated from the protease, and wherein the P-DPS, after conversion into plasmin, is not inhibited by α-2 antiplasmin, comprising contacting said P-DPS with a biological fluid, and determining the resulting plasmin produced from the P-DPS by the action of the PA activity.

5. A method as claimed in claim 4, wherein the protease digestion is carried out at pH 7–8.

6. A method as claimed in claim 4, wherein the protease digestion is carried out at pH 10–13.

7. A diagnostic assay employing a proteolytically-digested plasminogen source (P-DPS), wherein said D-PDS is generated by digesting a plasminogen with a protease and the P-DPS is separated from the protease, and wherein the P-DPS, after conversion into plasmin, is not inhibited by α-2 antiplasmin, comprising contacting said D-PDS with a biological fluid and measuring the resulting plasmin produced as a result of contact with the biological fluid.

8. A method for counteracting the inhibitory effect of α-2-antiplasmin on plasmin in an assay of PA activity in a biological fluid comprising proteolytically digesting plasminogen to form a substrate, wherein the digestion of the plasminogen to generate the proteolytically-digested plasminogen employs a protease.

* * * * *